United States Patent [19]

Arnold et al.

[11] Patent Number: 4,957,533
[45] Date of Patent: Sep. 18, 1990

[54] N-PHENYLALKYLBENZAMIDE FUNGICIDES

[75] Inventors: Wendell R. Arnold, Carmel; James D. Davenport, Indianapolis, both of Ind.

[73] Assignee: Eli Lilly and Company, Indianapolis, Ind.

[21] Appl. No.: 239,355

[22] Filed: Sep. 1, 1988

Related U.S. Application Data

[63] Continuation-in-part of Ser. No. 112,657, Oct. 26, 1987, abandoned.

[51] Int. Cl.$^5$ .................. A01N 37/18; A01N 9/20; C07C 103/76
[52] U.S. Cl. .................. 71/3; 514/599; 514/617; 514/633; 564/71; 564/185; 564/279
[58] Field of Search .................. 564/185, 74, 229; 514/617, 599, 633

[56] References Cited

U.S. PATENT DOCUMENTS 3,969,510  7/1976  Osieka et al. .................. 424/324

FOREIGN PATENT DOCUMENTS 680367 of 1967 Belgium.
0058657 4/1982 Japan .................. 564/185

OTHER PUBLICATIONS

Maybridge Chemical Company Ltd. "Structures List No. 135", 2/87.
Derwent Abstract 67-8046H, abstracting FR 1581075.
Derwent Abstract 67-08651H, abstracting J 28119/69.
Derwent Abstract 66-30622F, abstracting FR 1501151.
Derwent Abstract 66-01872F, abstracting GB 853295.
Derwent Abstract 77-80353Y, abstracting J 52116431.
Derwent Abstract 77-1039Y, abstracting J 51133243.
Derwent Abstract 77-84232Y, abstracting NL 7705037.
Chem. Abst. 62:16118e, abstracting Netherlands Patent Application 6,407,402.
Derwent Abstract 67-3996H abstracting BE 714356.
Derwent Abstract 66-29226F abstracting JA 20527/67.
Derwent Abstract 78-26132A abstracting J 53018732.
Derwent Abstracts 78-75425A abstracting J 53015444.
Derwent Abstract 81-87352D abstracting DD 150471.
Derwent Abstract 81-63427D abstracting J 56087501.
Derwent Abstract 83-839517 abstracting DE 3220883.
Derwent Abstract 83-839836 abstracting DE 3221673.
Derwent Abstract 73-13887U abstracting BE788983.
Derwent Abstract 75-68072W abstracting J 50083339.
Derwent Abstract 76-1270X abstracting NL 7506953.
Derwent Abstract 76-3704X abstracting US 3,929,879.
Derwent Abstract 76-17639X abstracting J 51007125.
Derwent Abstract 76-69428X abstracting J 51086124.
Derwent Abstract 82-84530E abstracting J 57139053.
Derwent Abstract 82-88822E abstracting J 57145348.
Derwent Abstract 83-702309 abstracting J 58088390.
Derwent Abstract 81-33574D abstracting J 56029552.
Derwent Abstract 73-45402U abstracting J 73026213.

Primary Examiner—Richard L. Raymond
Assistant Examiner—Raymond Covington
Attorney, Agent, or Firm—Donald R. Stuart; Leroy Whitaker

[57] ABSTRACT

Compounds of the formula (I):

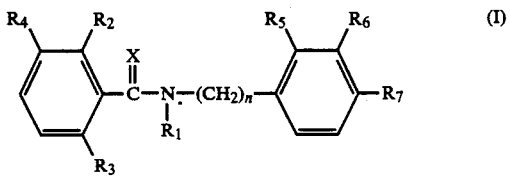

wherein:
  X=O, S, or NOH;
  $R^1$ is H or $CH_3$;
  n=1, 2, or 3;
  $R^2$, $R^3$, and $R^4$ are as defined in one of the following paragraphs
   (a) $R^2$ and $R^3$ are independently Cl or Br, and $R^4$ is H;
   (b) $R^2$, $R^3$ and $R^4$ are independently Cl or Br;
   (c) $R^2$ is F, $R^3$ is Cl, and $R^4$ is H; or
   (d) $R^2$ and $R^3$ are $CH_3$ or $C_2H_5$, and $R^4$ is H;
  $R^5$, $R^6$ and $R^7$ are as defined in one of the following paragraphs
   (a) one of $R^6$ and $R^7$ is $CF_3$, $R^5$ and the other of $R^6$ and $R^7$ is H;
   (b) $R^5$ and $R^6$ are H; and $R^7$ is F, Cl, or Br;
   (c) $R^5$ and $R^7$ are independently F, Cl or Br and $R^6$ is H;
   (d) $R^5$ and $R^6$ are independently F, Cl, or Br, and $R^7$ is H;
   (e) $R^6$ and $R^7$ are independently F, Cl, or Br, and $R^5$ is H; or
   (f) $R^6$ is phenoxy and $R^5$ and $R^7$ are H are plant fungicides. Combinations, compositions, and fungicidal methods employing the compounds of formula (I) are also provided.

24 Claims, No Drawings

N-PHENYLALKYLBENZAMIDE FUNGICIDES

RELATED APPLICATION

This is a continuation-in-part of Ser. No. 07/112,657, filed Oct. 26, 1987, now abandoned.

BACKGROUND OF THE INVENTION

1. Field of the Invention

This invention provides fungicide compounds, fungicide combinations, fungicide compositions, and fungicide methods.

The fungicide compounds of the invention are useful in combating plant fungal diseases, particularly powdery mildew of cereal grain crops. The mechanism of action, although not yet fully understood, appears to differ from that of currently used fungicides.

Combinations of the compounds of the invention with other fungicides provide products to which disease organisms are less likely to develop resistance. In addition, some of the combinations have synergistic activity.

2. State of the Art

French patent No. 1,581,075 discloses certain N-phenylmethylbenzamides that are substituted with chlorine on both rings. The disclosed compounds are alleged to have antifungal, antibacterial and herbicidal properties.

SUMMARY OF THE INVENTION

More particularly, the invention provides compounds of the formula (I):

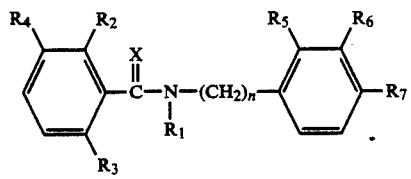

wherein:
- X = O, S, or NOH;
- $R^1$ is H or $CH_3$;
- n = 1, 2, or 3;
- $R^2$, $R^3$, and $R^4$ are as defined in one of the following paragraphs
  - (a) $R^2$ and $R^3$ are independently Cl or Br, and $R^4$ is H;
  - (b) $R^2$, $R^3$ and $R^4$ are independently Cl or Br;
  - (c) $R^2$ is F, $R^3$ is Cl, and $R^4$ is H; or
  - (d) $R^2$ and $R^3$ are $CH_3$ or $C_2H_3$, and $R^4$ is H;
- $R^5$, $R^6$ and $R^7$ are as defined in one of the following paragraphs
  - (a) one of $R^6$ and $R^7$ is $CF_3$, $R^5$ and the other of $R^6$ and $R^7$ is H;
  - (b) $R^5$ and $R^6$ are H; and $R^7$ is F, Cl, or Br;
  - (c) $R^5$ and $R^7$ are independently F, Cl or Br and $R^6$ is H;
  - (d) $R^5$ and $R^6$ are independently F, Cl, or Br, and $R^7$ is H;
  - (e) $R^6$ and $R^7$ are independently F, Cl, or Br, and $R^5$ is H; or
  - (f) $R^6$ is phenoxy and $R^5$ and $R^7$ are H.

The fungicidal combinations of the invention comprise at least 1% by weight of a compound of formula (I) in combination with a second fungicidal compound.

The fungicidal compositions of the invention comprise a compound of formula (I) in combination with a phytologically-acceptable carrier.

The fungicidal method of the invention comprises applying a fungus inhibiting amount of a compound or combination of the invention to the locus of a fungus.

DETAILED DESCRIPTION OF THE INVENTION

Throughout this document, all temperatures are given in degrees Celsius, and all percentages are weight percentages unless otherwise stated.

Compounds

While all of the compounds of the invention are useful fungicides, certain classes are preferred, i.e.

(1) compounds of formula (Ia):

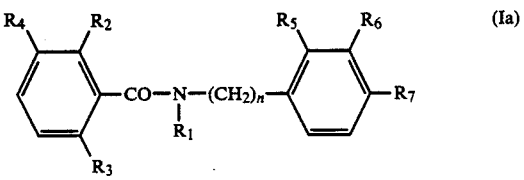

wherein:
- $R^1$ is H or $Ch_3$;
- n = 1, 2, or 3;
- $R^2$, $R^3$, and $R^4$ are as defined in one of the following paragraphs
  - (a) $R^2$ and $R^3$ are Cl, and $R^4$ is H;
  - (b) $R^2$, $R^3$ and $R^4$ are Cl; or
  - (c) $R^2$ is F, $R^3$ is Cl, and $R^4$ is H;
- $R^5$, $R^6$ and $R^7$ are as defined in one of the following paragraphs
  - (a) one of $R^6$ and $R^7$ is $CF_3$, $R^5$ and the other of $R^6$ and $R^7$ is H;
  - (b) $R^5$ and $R^6$ are H; and $R^7$ is F, Cl, or Br;
  - (c) $R^5$ and $R^7$ are independently F, Cl or Br and $R^6$ is H;
  - (d) $R^5$ and $R^7$ are independently F, Cl, or Br, and $R^6$ $R^7$ is H;
  - (e) $R^6$ and $R^7$ are independently F, Cl, or Br, and $R^5$ is H; or
  - (f) $R^6$ is phenoxy and $R^5$ and $R^7$ are H.

(2) compounds of formula (Ia) wherein $R^1$ is H;

(3) compounds of formula (Ia) wherein $R^2$ and $R^3$ are Cl and $R^4$ is H;

(4) compounds of formula (Ia) wherein $R^6$ is $CF_3$;

(5) compounds of formula (Ia) wherein $R^6$ is phenoxy;

(6) compounds of formula (Ia) wherein $R^7$ is $CF_3$.

Of the compounds tested, 2,6-dichloro-N-[[4-(trifluoromethyl)-phenyl]methyl]benzamide is the most preferred compound.

Synthesis

The amides of formula (I), wherein X is O, are readily prepared by the reaction of a benzoylchloride of the formula:

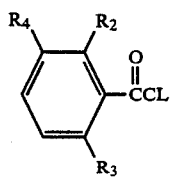

with an aralkylamine of the formula (III):

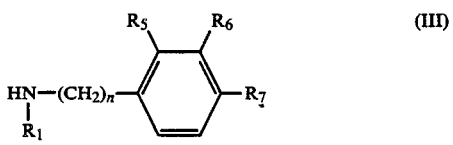

wherein $R^1$, $R^2$, $R^3$, $R^4$, $R^5$, $R^6$, and $R^7$ are as defined above. The reaction is well known in the art and is conveniently conducted with equimolar amounts of reactants in organic solvents such as toluene, benzene, or tetrahydrofuran. An organic base such as triethylamine or pyridine may usefully be included in the reaction mixture to act as an acid scavenger. Reaction temperatures may range from 10° to 120° C. Typically the reaction is carried out either at room temperature or at the reflux temperature. The salts formed are removed by washing with water or by filtration, and the solvent is removed by distillation. The product is then recrystallized from an appropriate solvent or solvent mixture, such as ethanol/water or hexane/ethylacetate.

The benzoylchlorides of formula (II) and the aralkylamines of formula (III) are commercially available or are readily prepared using known procedures. The phenethylamines and phenylpropylamines of formula (III) can be prepared, for example, by reducing the corresponding nitrile. A suitable procedure is given in *J. Org. Chem.* 1981, 46, 4252–4258. The required nitriles are prepared using commonly known procedures.

Thioamides of formula (I), wherein X is S, are prepared by reacting an amide of formula (I), wherein X is O, with Lawesson's reagent, the dimer of p-methoxyphenylthionophosphine sulfide, as described in S. Raucher and P. Klein, *Tetrahedron Letters*, Vol. 21, pp 4061–64 (1980). The reaction is typically carried out with an equivalent or excess amount of Lawesson's reagent in an organic solvent. Typical solvents are toluene and xylene. The reaction temperature is not critical, and room temperature or reflux temperature is typically used for convenience.

Amidines of formula (I), wherein X is NOH, can be prepared by reacting an N-hydroxybenzimidoyl chloride of formula (IV):

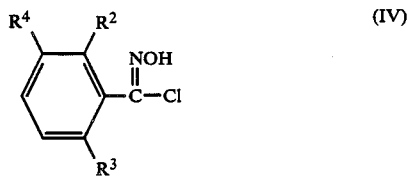

with an aralkylamine of formula (III), using reaction conditions like those used in preparation of the amides of formula (I).

The N-hydroxybenzimidoyl chlorides of formula (IV) are prepared using conventional procedures.

The following working examples further illustrate the synthesis of the compounds of the invention.

PREPARATION 1

3-(Trifluoromethyl)benzeneethanamine

Following the procedure of *J. Org. Chem.* 1981, 46, 4252–4258, 16.6 g (0.09 mole) of 3-(trifluoromethyl)benzonitrile was reduced to provide the title compound. More specifically, 4.3 g (0.11 mole) of LiAlH$_4$, and 15 g of AlCl$_3$ were added to 300 ml of ethyl ether. The combined mixture was refluxed for 16 hours, then cooled to 0°, after which 30 ml of water and about 50 ml of 30M potassium hydroxide solution were then added. The product was extracted from the mixture into ethyl ether (4×300 ml), and the ether was then dried over Na$_2$SO$_4$, filtered, and stripped to dryness, giving 14 g of the title product.

4-(Triffuoromethyl)benzeneethanamine was prepared using the same procedure.

PREPARATION 2

4-(Trifluoromethyl)benzenepropanamine

Catalytic (10% Pd/C) hydrogenation of 5 g of trans-4-(trifluoromethyl)cinnamic acid in ethyl alcohol produced a solid (4-(trifluoromethyl)benzenepropanoic acid), to which excess SOCl$_2$ was added to produce the acid chloride. The mixture was warmed on a steam bath for one-half hour. The solvent was evaporated, then toluene and concentrated ammonium hydroxide were added, to produce 4-(trifluoromethyl)benzenepropanamide. This was dehydrated by adding excess SOCl$_2$ and warming on a steam bath for one-half hour to give 4-(trifluoromethyl)benzenepropanenitrile, which was catalytically (Pd/C) hydrogenated to provide the title compound.

PREPARATION 3

N-Methyl-4-(trifluoromethyl)benzylamine

Methylamine was passed into a solution of about 10.1 g of 4-(trifluoromethyl)benzaldehyde in about 100 ml of benzene over MgSO$_4$ for four hours with stirring. The solution was filtered, and then the solvent was evaporated to give N-[4-(trifluoromethyl)benzylidene]methylamine as an oil. This was taken up in benzene and catalytically (5% Pd/C) hydrogenated to give the title product.

PREPARATION 4

2,6-dichloro-N-hydroxybenzimidoyl chloride

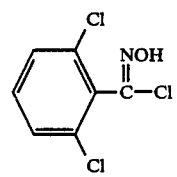

2,6-dichlorobenzoldehyde (15 g) was reacted with an equivalent amount of hydroxylamine hydrochloride at reflux in a mixture of ethylalcohol and water. The reaction mixture was then washed with sodium bicarbonate, and the oxime product was extracted into chloroform. The solution of the oxime in chloroform was cooled to −7° C. and kept below 5° C. while it was stirred and chlorine gas was bubbled into it for four hours (until the blue color disappeared). The chloroform and excess chlorine were removed by reducing the pressure. Yield 19 grams.

EXAMPLE 1

2,6-Dichloro-N-[[4-(trifluoromethyl)phenyl]-methyl]-benzamide

To 21.1 g (0.1 mole) of 4-trifluoromethylbenzylamine hydrochloride was added 20.9 g (0.10 mole) of 2,6-dichlorobenzoyl chloride in 200 ml of tetrahydrofuran. Then was added in 1 portion 30 ml triethylamine.

The mixture was refluxed for 1 hour, cooled, and filtered to remove triethylamine hydrochloride. The filtrate was evaporated to dryness and the residue was recrystallized from an ethyl acetate/hexane mixture to give 31 g (93%) yield. M.P. 135°–136°.

EXAMPLES 2–6

The compounds of Examples 2–6 were prepared by mixing 1 g of the appropriate benzylamine hydrochloride with 2 g of 2,6-dichlorobenzoyl chloride in a 1:1 by volume mixture of triethylamine and tetrahydrofuran and allowing the mixture to stand for a period that ranged from 2 to 6 weeks. Work up typically consisted of adding water, extracting the product into CHCl₃, and chormatographing over a 10′×½″ Merk 60 silica gel column using a hexame EtOAc gradient, and then recrystallizing the product from an ethylacetate/hexane mixture.

| Ex. | Compound | Yield | M.P. |
|---|---|---|---|
| 2 | 2,6-Dichloro-N-[[3-(trifluoromethyl)phenyl]methyl]benzamide | 80% | 98–100° |
| 3 | 2,6-Dichloro-N-[(4-bromophenyl)methyl]benzamide | 62% | N.A. |
| 4 | 2,6-Dichloro-N-[(3-phenoxy-phenyl)methyl]benzamide | 90% | 127–129° |
| 5 | 2,6-Dichloro-N-[(2,3-dichlorophenyl)methyl]benzamide | 56 | 183–185° |
| 6 | 2,6-Dichloro-N-[(4-fluorophenyl)methyl]benzamide | 54% | 152–154° |

EXAMPLES 7–8

The compounds of Examples 7 and 8 were prepared by reacting equimolar amounts of 2,6-dichlorobenzoylchloride and the appropriate aralkylamine in a 1:1 by volume mixture of triethylamine and toluene at reflux for 20 minutes, washing with water, extracting with CHCl₃, evaporating to dryness, and recrystallizing in an acetone/hexane solution.

| Ex. | Compound | Yield | M.P. |
|---|---|---|---|
| 7 | 2,6-Dichloro-N-[(3,4-dichlorophenyl)methyl]benzamide | 74% | 180–182° |
| 8 | 2,6-Dichloro-N-[[4-(trifluoromethyl)phenyl]methyl]benzamide | | 135–136° |

EXAMPLE 9

2,6-Dichloro-N-(4-chlorophenyl)methyl]benzamide

The title compound was prepared using essentially the same procedure as that for Examples 7–8, except that the solvent used was a 1:1 mixture of ethyl acetate and triethylamine. Yield: 24%. M.P. 170°–172°.

EXAMPLES 10–16

The compounds of Examples 10 to 16 were prepared by reacting equimolar amounts of the approximately substituted benzoylchloride and the approximately substituted aralkylamine in a 1:1 by volume mixture of triethylamine and tetrahydrofuran at reflux for from 10 minutes to 1 hour.

| Ex. | Compound | Yield | M.P. |
|---|---|---|---|
| 10 | 2,6-Dichloro-N-[(2-chloro-4-fluorophenyl)methyl]benzamide | 88% | 138–140° |
| 11 | 2,6-Dichloro-N-[3-[4-(trifluoromethyl)phenyl]propyl]benzamide | 31% | 109–111° |
| 12 | 2,6-Dichloro-N-[2-[3-(trifluoromethyl)phenyl]ethyl]benzamide | 53% | 109–110° |
| 13 | 2,6-Dichloro-N-methyl-N-[[4-(trifluoromethyl)phenyl]methyl]benzamide | 71% | N/A |
| 14 | 2-Chloro-6-fluoro-N-[[4-(trifluoromethyl)phenyl]methyl]benzamide | 82% | 104–105° |
| 15 | 2,3,6-Trichloro-N-[[4-(trifluoromethyl)phenyl]methyl]benzamide | 30% | N/A |
| 16 | 2,3,6-Trichloro-N-[[3-(trifluoromethyl)phenyl]methyl]benzamide | 37% | N/A |

EXAMPLE 17

N²-hydroxy-N:-(4-trifluoromethylphenylmethyl)-2,6-dichlorophenylamidine

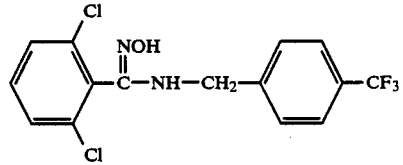

To a solution comprising 19 g of the compound of Preparation 4 in THF was added 19 g of (4-trifluoromethylphenylmethyl)amine hydrochloride, followed by 50 ml of triethylamine. The mixture was heated to reflux for two hours, then filtered. The solid was washed with THF, then the THF fractions were combined and evaporated to dryness. The product was chromatographed on a silica gel column (½″×20 ft), yielding 6 g of the title product. M.P. 162°–164° C.

EXAMPLE 18

2,6-diethyl-N-[4-(trifluoromethyl)phenyl]methyl]benzenecarbothioamide

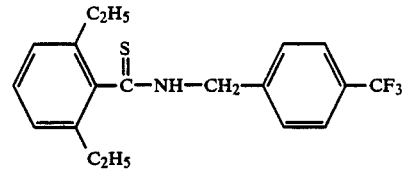

To 3.6 g of 2,6-diethyl-N-[[4-(trifluoromethyl)phenyl]methyl]benzamide in toluene was added 5 g of Lawesson's reagent. The mixture was heated to reflux. When the reaction was complete, as shown by TLC, the mixture was cooled and eluted over silica gel using 25% ethylacetate in hexane. Yield 1.3 g. M.P. 125°–127° C.

Utility

The compounds of the present invention have been found to control fungi, particularly powdery mildew of cereal crops such as wheat and barley. When employed in the treatment of plant fungal diseases, the compounds are applied to the plants in a disease inhibiting and non-herbicidal amount. The term "disease inhibiting and non-herbicidal amount," as used herein, refers to an amount of a compound of the invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the method of application, the particular plant species, climate conditions and the like. The compounds of the invention may also be used to protect stored grain and other non-plant loci from fungal infestation.

Greenhouse Tests

The following experiments were performed in the laboratory to determine the fungicidal efficacy of the compounds of the invention.

TEST 1

This screen was used to evaluate the efficacy of the present compounds against a variety of different organisms that cause plant diseases.

The test compounds were formulated for application by dissolving 50 mg of the compound into 1.25 ml of solvent. The solvent was prepared by mixing 50 ml of Tween 20 with 475 ml of acetone and 475 ml of ethanol. The solvent/compound solution was diluted to 125 ml with deionized water. The resulting formulation contains 400 ppm test chemical. Lower concentrations were obtained by serial dilution with the solvent-surfactant mixture.

The formulated test compounds were applied by foliar spray. The following plant pathogens and their corresponding plants were employed.

| Pathogen | Designation in Following Tables | Host |
|---|---|---|
| Erysiphe graminis tritici (powdery mildew) | POWD MDEW | wheat |
| Pyricularia oryzae (rice plast) | RICE BLAS | rice |
| Puccinia recondita tritici (leaf rust) | LEAF RUST | wheat |
| Botrytis cinerea (gray mold) | GRAY MOLD | grape berries |
| Pseudoperonospora cubensis (downy mildew) | DOWN MDEW | squash |
| Cercospora beticola (leaf spot) | LEAF SPOT | sugar beet |
| Venturia inaequalis (apple scab) | APPL SCAB | apple seedling |
| Septoria tritici (leaf blotch) | LEAF BLOT | wheat |

The formulated technical compounds were sprayed on all foliar surfaces of the host plants (or cut berry) to past run-off. Single pots of each host plant were placed on raised, revolving pedestals in a fume hood. Test solutions were sprayed on all foliar surfaces. All treatments were allowed to dry and the plants were inoculated with the appropriate pathogens within 2–4 hours.

The effectiveness of test compounds in controlling disease was on a 1–9 scale. These ratings represent the following percent disease control:
1=0–19%, 2=20–29%, 3=30–39%, 4=40–59%, 5=60–74%, 6=75–89%, 7=90–96%, 8=97–99% and 9=100%.

Also a phytotoxicity rating was recorded when apparent, using a scale from 1 to 5 wherein 1 indicates no toxicity and 5 indicates death to the plant. Finally, where phytotoxicity was present, a letter rating may be given to the plant indicating the type of injury caused to the plant. These injuries were coded as follows:

G=General necrosis
W=Wilting
S=Stunting
C=Chlorosis
F=Formative

Table I presents the activity of typical compounds of the present invention when evaluated in this experiment:

TABLE 1

| EX. NO. | PPM | POWD MDEW | RICE BLAS | LEAF RUST | GRAY MOLD | DOWN MDEW | LEAF SPOT | APPL SCAB | LEAF BLOT |
|---|---|---|---|---|---|---|---|---|---|
| 1 | 400 | 8 | 8 | | | | | | |
| | | 7 | | | | 62G | | | |
| | | 7 | 3 | 1 | 1 | 1 | | | |
| | | 8 | | | | | | | |
| | | 82C | 6 | 1 | 1 | 1 | | | |
| | 100 | 7 | 6 | | | | 1 | 1 | 1 |
| | | 6 | | | | 5 | 3 | 1 | 1 |
| | | 8 | | | | | | | |
| | | 8 | | | | | 1 | 1 | 7 |
| | | 8 | | | | | | | 5 |
| | 25 | 7 | 1 | | | | | | |
| | | 4 | | | | 2 | | | |
| | | 6 | | | | | | | |
| | | 6 | | | | | | | |
| | | 7 | | | | | | | 1 |
| | | 7 | | | | | | | 1 |
| | 6.25 | 4 | | | | | | | |
| | | 6 | | | | | | | 1 |
| | | 5 | | | | | | | 1 |
| | 1.56 | 2 | | | | | | | 1 |
| 2 | 400 | 7 | 1 | 1 | 1 | 1 | | | |
| | | 7 | | | | | | | |
| | 100 | 6 | | | | | 1 | 1 | 5 |
| | 25 | 3 | | | | | | | |

TABLE 1-continued

| EX. NO. | PPM | POWD MDEW | RICE BLAS | LEAF RUST | GRAY MOLD | DOWN MDEW | LEAF SPOT | APPL SCAB | LEAF BLOT |
|---|---|---|---|---|---|---|---|---|---|
| 3 | 400 | 5 | 1 | 1 | 1 | 1 | | | |
| 4 | 400 | 7 | 4 | 5 | 1 | 7 | | | |
| 5 | 400 | 72C | 1 | 1 | 1 | 1 | | | |
| | | 6 | | | | | | | |
| | 100 | 5 | | | | | 1 | 3 | 1 |
| | 25 | 2 | | | | | | | |
| 6 | 400 | 4 | 1 | 1 | 1 | 1 | | | |
| 7 | 400 | 52G | 1 | 5 | 1 | 1 | | | |
| | 100 | 42G | 1 | 3 | 1 | 1 | 5 | 1 | 1 |
| | 25 | 1 | 1 | 1 | 1 | 1 | | | |
| 9 | 400 | 6 | 1 | 12C | 1 | 1 | | | |
| 10 | 400 | 7 | 1 | 1 | 1 | 1 | | | |
| | | 5 | | | | | | | |
| | 100 | 4 | | | | | 1 | 1 | 1 |
| | 25 | 2 | | | | | | | |
| 11 | 400 | 7 | 4 | 1 | 1 | 1 | | | |
| | | 8 | | | | | | | |
| | 100 | 7 | | | | | 2 | 6 | 7 |
| | | 7 | | | | | | | 3 |
| | 25 | 6 | | | | | | | |
| | | 5 | | | | | | | 1 |
| | 6.25 | 2 | | | | | | | 1 |
| 12 | 400 | 72C | 1 | 1 | 1 | 1 | | | |
| | | 5 | | | | | | | |
| | 100 | 2 | | | | | .6 | 1 | 6 |
| | 25 | 1 | | | | | | | |
| 13 | 400 | 8 | 1 | 1 | 1 | 1 | | | |
| | | 6 | | | | | | | |
| | 100 | 5 | | | | | 4 | 1 | 6 |
| | 25 | 1 | | | | | | | |
| 14 | 400 | 8 | | | | | | | |
| | | 8 | 6 | 1 | 1 | 6 | | | |
| | 100 | 7 | | | | | 7 | 6 | 5 |
| | | 7 | | | | | 1 | | |
| | 25 | 5 | | | | | | | |
| | | 4 | | | | | 1 | | |
| | 6.25 | 2 | | | | | 1 | | |
| 15 | 400 | 6 | 4 | 62G | 1 | 72G | | | |
| | | | | | | 3 | | | |
| | 100 | | | | | 1 | 1 | 1 | 5 |
| | 25 | | | | | 1 | | | |
| 16 | 400 | 82G | 1 | 62C | 1 | 52C | | | |
| | | 92G | | | | | | | |
| | 100 | 9 | | | | | 6 | 1 | 4 |
| | | 8 | | | | | | | |
| | 25 | 9 | | | | | | | |
| | | 5 | | | | | | | |
| | 6.25 | 4 | | | | | | | |
| 17 | 400.00 | 3 | 1 | 4 | 1 | 8 | | | |
| | | | | | | 8 | | | |
| | 100.00 | | | | | 8 | | | |
| | | | | | | 4 | | | |
| | 25.00 | | | | | 1 | | | |
| | | | | | | 3 | | | |
| | 6.25 | | | | | 1 | | | |
| 18 | 400.00 | 3 | 3 | 4 | 1 | 3 | | | |

TEST 2

The compound of Example 1 was evaluated against powdery mildew (*Erysiphe graminis*) of wheat and barley under greenhouse conditions. The compound was dissolved in a 1:1 mixture of acetone:ethanol containing 1% Tween 20. Spray solutions were made up in distilled water containing 0.05% Tween 20. Wheat and barley plants (about 10 cm) were sprayed to runoff with a DeVilbiss handsprayer. To evaluate protectant activity, plants were treated 4, 2, or 1 days before they were inoculated with powdery mildew. To evaluate curative activity, plants were treated 1, 2, or 4 days after they were inoculated. To evaluate eradicant activity, plants were treated 5 or 6 days after they were inoculated. Inoculation comprised dusting with spores from infected plants. Four days after control plants were inoculated, developing disease could be observed under the plant cuticle. Five days after inoculation the surface mycelia were appearing; by 6 days post-inoculation the mycelia were well developed but conidia were not yet being released.

Plants were maintained in a greenhouse at 16°–19° C. under a 16 hours light: 8 hours dark cycle.

Untreated control plants, inoculated at the same time as the test plants, were evaluated for extent of disease 7 and 14 days after inoculation. The percentage of disease control obtained in the treated plants was also evaluated 7 and 14 days after inoculation.

Tables 2 to 7 report results of this test. The data demonstrates that 2,6-dichloro-N-[[4-(trifluoromethyl)-phenyl]methyl]benzamide has excellent protectant, curative, and eradicant activity against powdery mildew of barley and wheat.

TABLE 2

PROTECTANT ACTIVITY OF 2,6-DICHLORO-N-[[4-(TRIFLUOROMETHYL)PHENYL]METHYL] BENZAMIDE AGAINST *ERYSIPHE GRAMINIS* OF BARLEY

| | Percent Disease Control | | | | | |
|---|---|---|---|---|---|---|
| Treatment (days before inoculation) | 1 | 2 | 4 | 1 | 2 | 4 |
| Evaluation (days after inoculation) | 7 | 7 | 7 | 14 | 14 | 14 |
| Application Rate (ppm) | | | | | | |
| 1.56 | 54 | 58 | 62 | 40 | 18 | 13 |
| 6.25 | 100 | 100 | 69 | 80 | 59 | 75 |
| 25.0 | 100 | 100 | 97 | 85 | 79 | 93 |
| Control Disease (%) | 38 | 38 | 25 | 63 | 46 | 43 |

TABLE 3

PROTECTANT ACTIVITY OF 2,6-DICHLORO-N-[[4-(TRIFLUOROMETHYL)PHENYL]METHYL] BENZAMIDE AGAINST *ERYSIPHE GRAMINIS* OF WHEAT

| | Percent Disease Control | | | | | |
|---|---|---|---|---|---|---|
| Treatment (days before inoculation) | 1 | 2 | 4 | 1 | 2 | 4 |
| Evaluation (days after inoculation) | 7 | 7 | 7 | 14 | 14 | 14 |
| Application Rate (ppm) | | | | | | |
| 1.56 | 67 | 33 | 19 | 22 | 31 | 25 |
| 6.25 | 79 | 83 | 43 | 61 | 42 | 0 |
| 25.0 | 94 | 83 | 71 | 77 | 77 | 50 |
| Control Disease (%) | 38 | 38 | 27 | 40 | 54 | 38 |

TABLE 4

CURATIVE ACTIVITY OF 2,6-DICHLORO-N-[[4-(TRIFLUOROMETHYL)PHENYL]METHYL] BENZAMIDE AGAINST *ERYSIPHE GRAMINIS* OF BARLEY

| | Percent Disease Control | | | | | |
|---|---|---|---|---|---|---|
| Treatment (days after inoculation) | 1 | 2 | 4 | 1 | 2 | 4 |
| Evaluation (days after inoculation) | 7 | 7 | 7 | 14 | 14 | 14 |
| Application Rate (ppm) | | | | | | |
| 1.56 | 17 | 33 | 58 | 70 | 23 | 13 |
| 6.25 | 81 | 90 | 67 | 70 | 79 | 75 |
| 25.0 | 100 | 100 | 79 | 100 | 100 | 98 |
| Control Disease (%) | 38 | 38 | 38 | 43 | 60 | 51 |

TABLE 5

CURATIVE ACTIVITY OF 2,6-DICHLORO-N-[[4-(TRIFLUOROMETHYL)PHENYL]METHYL] BENZAMIDE AGAINST *ERYSIPHE GRAMINIS* OF WHEAT

| | Percent Disease Control | | | | | |
|---|---|---|---|---|---|---|
| Treatment (days after inoculation) | 1 | 2 | 4 | 1 | 2 | 4 |
| Evaluation (days after inoculation) | 7 | 7 | 7 | 14 | 14 | 14 |
| Application Rate (ppm) | | | | | | |
| 1.56 | 42 | 94 | 68 | 58 | 46 | 72 |
| 6.25 | 100 | 100 | 84 | 91 | 99 | 100 |
| 25.0 | 100 | 100 | 100 | 100 | 99 | 100 |
| Control Disease (%) | 38 | 38 | 15 | 63 | 63 | 33 |

TABLE 6

ERADICANT ACTIVITY OF 2,6-DICHLORO-N-[[4-(TRIFLUOROMETHYL)PHENYL]METHYL] BENZAMIDE AGAINST *ERYSIPHE GRAMINIS* OF BARLEY

| | Percent Disease Control Method 1* | | Percent Disease Control Method 2** | |
|---|---|---|---|---|
| Treatment (days after inoculation) | 5 | 6 | 5 | 6 |
| Application Rate (ppm) | | | | |
| 6.25 | 74 | 72 | 82 | 81 |
| 25.0 | 84 | 55 | 89 | 75 |
| 50.0 | 92 | 55 | 92 | 73 |
| Control Disease (%) | 59 | 53 | 59 | 53 |

*Method 1: Percent disease control derived from rating overall (living and dead) disease on leaf surface.
**Method 2: Percent disease control derived from rating overall cover of dead and living mildew minus percent of overall mildew cover that was dead.

TABLE 7

ERADICANT ACTIVITY OF 2,6-DICHLORO-N-[[4-(TRIFLUOROMETHYL)PHENYL]METHYL] BENZAMIDE AGAINST *ERYSIPHE GRAMINIS* OF WHEAT

| | Percent Disease Control Method 1* | | Percent Disease Control Method 2** | |
|---|---|---|---|---|
| Treatment (days after inoculation) | 5 | 6 | 5 | 6 |
| Application Rate (ppm) | | | | |
| 6.25 | 94 | 82 | 94 | 87 |
| 25.0 | 94 | 73 | 94 | 82 |
| 50.0 | 100 | 77 | 100 | 90 |
| Control Disease (%) | 36 | 34 | 36 | 34 |

*Method 1: Percent disease control derived from rating overall (living and dead) disease on leaf surface.
**Method 2: Percent disease control derived from rating overall cover of dead and living mildew minus percent of overall mildew cover that was dead.

TEST 3

The compounds of Examples 1 and 11-16 were further tested in the greenhouse against powdery mildew (*Erysiphe graminis tritici*) of wheat using a test method in which the time of application of the compound and the time of inoculation were varied with respect to each other, to evaluate protective and curative disease control. In the table below, the time given is the number of hours elapsing between treatment and inoculation. A negative time indicates that the pathogen was inoculated before treatment. In this case, curative activity was tested. A positive time indicates that the plants were treated before they were inoculated with pathogen. In this case, protectant activity was tested.

The compounds were formulated and applied as foliar sprays as in Test 1. The results were evaluated on the 1-9 rating scale described in Test 1. Results are given in Table 8.

TABLE 8

Foliar Application
Powdery Mildew of Wheat

| Compound | Time in Hours | Rate in ppm | Disease Control Rating |
|---|---|---|---|
| Example 1 | −72 | 100.00 | 9.0 |
| | | | 8.0 |
| | | | 9.0 |
| | | | 9.0 |
| | | | 9.0 |
| | | | 6.0 |

TABLE 8-continued

Foliar Application
Powdery Mildew of Wheat

| Compound | Time in Hours | Rate in ppm | Disease Control Rating |
|---|---|---|---|
|  |  |  | 8.5 |
|  |  | 50.00 | 9.0 |
|  |  |  | 8.0 |
|  |  |  | 9.0 |
|  |  |  | 9.0 |
|  |  |  | 9.0 |
|  |  |  | 6.0 |
|  |  |  | 9.0 |
|  |  |  | 9.0 |
|  |  |  | 8.5 |
|  |  |  | 8.0 |
|  |  | 25.00 | 7.0 |
|  |  |  | 5.0 |
|  |  |  | 9.0 |
|  |  |  | 8.0 |
|  |  |  | 9.0 |
|  |  |  | 8.5 |
|  |  |  | 9.0 |
|  |  |  | 6.0 |
| Example 1 | −72 | 25.00 | 9.0 |
|  |  |  | 8.5 |
|  |  |  | 8.5 |
|  |  |  | 8.0 |
|  |  | 12.50 | 5.0 |
|  |  |  | 5.0 |
|  |  |  | 9.0 |
|  |  |  | 7.0 |
|  |  |  | 9.0 |
|  |  |  | 8.0 |
|  |  |  | 8.0 |
|  |  |  | 5.0 |
|  |  |  | 9.0 |
|  |  |  | 8.0 |
|  |  |  | 8.5 |
|  |  |  | 7.0 |
|  |  | 6.25 | 4.0 |
|  |  |  | 7.5 |
|  |  | 6.12 | 5.0 |
|  |  | 3.12 | 5.5 |
|  | −50 | 6.25 | 5.0 |
|  |  | 3.12 | 3.0 |
|  | −48 | 100.00 | 8.0 |
|  |  | 50.00 | 8.0 |
|  |  | 25.00 | 7.0 |
|  |  | 12.50 | 7.0 |
| Example 1 | −24 | 100.00 | 9.0 |
|  |  |  | 9.0 |
|  |  |  | 9.0 |
|  |  |  | 9.0 |
|  |  |  | 9.0 |
|  |  |  | 9.0 |
|  |  | 50.00 | 8.5 |
|  |  |  | 8.0 |
|  |  |  | 9.0 |
|  |  |  | 9.0 |
|  |  |  | 9.0 |
|  |  |  | 9.0 |
|  |  |  | 8.5 |
|  |  | 25.00 | 8.5 |
|  |  |  | 8.0 |
|  |  |  | 8.5 |
|  |  |  | 8.5 |
|  |  |  | 9.0 |
|  |  |  | 9.0 |
|  |  |  | 8.5 |
|  |  | 12.50 | 8.5 |
|  |  |  | 8.0 |
|  |  |  | 8.5 |
|  |  |  | 8.0 |
|  |  |  | 9.0 |
| Example 1 | −24 | 12.50 | 8.5 |
|  |  |  | 8.5 |
|  | 4 | 100.00 | 8.0 |
|  |  | 50.00 | 8.0 |
|  |  | 25.00 | 7.0 |
|  |  |  | 8.5 |
|  |  | 12.50 | 6.0 |
|  |  |  | 7.0 |
|  |  | 6.25 | 6.0 |
|  | 24 | 100.00 | 7.0 |
|  |  |  | 8.0 |
|  |  |  | 7.0 |
|  |  |  | 7.0 |
|  |  |  | 6.5 |
|  |  | 50.00 | 7.0 |
|  |  |  | 7.5 |
|  |  |  | 6.0 |
|  |  |  | 6.0 |
|  |  |  | 6.0 |
|  |  |  | 6.5 |
|  |  | 25.00 | 6.0 |
|  |  |  | 7.0 |
|  |  |  | 5.0 |
| Example 1 | 24 | 25.00 | 5.0 |
|  |  |  | 5.0 |
|  |  |  | 6.0 |
|  |  | 12.50 | 6.0 |
|  |  |  | 7.0 |
|  |  |  | 5.0 |
|  |  |  | 4.0 |
|  |  |  | 5.0 |
|  |  |  | 5.5 |
|  |  | 6.25 | 5.0 |
|  |  | 3.12 | 5.0 |
|  | 48 | 100.00 | 5.0 |
|  |  | 50.00 | 2.0 |
|  |  | 25.00 | 1.0 |
|  |  | 12.50 | 2.0 |
|  | 72 | 100.00 | 1.0 |
|  |  |  | 5.0 |
|  |  |  | 6.0 |
|  |  |  | 4.0 |
|  |  |  | 3.0 |
|  |  | 50.00 | 1.0 |
|  |  |  | 5.0 |
|  |  |  | 4.0 |
|  |  |  | 3.0 |
|  |  |  | 5.0 |
| Example 1 | 72 | 25.00 | 1.0 |
|  |  |  | 2.0 |
|  |  |  | 3.0 |
|  |  |  | 4.0 |
|  |  |  | 1.0 |
|  |  |  | 1.0 |
|  |  |  | 2.0 |
|  |  |  | 1.0 |
|  |  |  | 1.0 |
|  |  |  | 3.0 |
|  |  |  | 2.0 |
|  |  |  | 2.0 |
|  |  | 12.50 | 3.0 |
|  |  |  | 4.0 |
|  |  |  | 1.0 |
|  |  |  | 1.0 |
|  |  |  | 1.0 |
|  |  |  | 1.0 |
|  |  |  | 2.0 |
|  |  |  | 3.0 |
|  |  |  | 2.0 |
|  |  |  | 1.0 |
|  |  | 6.25 | 3.0 |
|  |  |  | 1.0 |
|  |  | 6.12 | 4.0 |
|  |  | 3.12 | 1.0 |
| Example 11 | −48 | 100.00 | 5.0 |
|  |  | 50.00 | 1.0 |
|  |  | 25.00 | 1.0 |
|  | −24 | 100.00 | 7.0 |
|  |  | 50.00 | 2.0 |
|  |  | 25.00 | 1.0 |
|  |  | 12.50 | 1.0 |
|  | 4 | 100.00 | 8.0 |

TABLE 8-continued

Foliar Application
Powdery Mildew of Wheat

| Compound | Time in Hours | Rate in ppm | Disease Control Rating |
|---|---|---|---|
| | | 50.00 | 6.0 |
| | | 25.00 | 2.0 |
| | | 12.50 | 1.0 |
| | 48 | 100.00 | 3.0 |
| | | 50.00 | 1.0 |
| | | 25.00 | 1.0 |
| | | 12.50 | 1.0 |
| Example 12 | −72 | 100.00 | 8.5 |
| | | 50.00 | 8.0 |
| | | 25.00 | 7.0 |
| | | 12.50 | 6.5 |
| Example 12 | −24 | 100.00 | 9.0 |
| | | 50.00 | 8.5 |
| | | 25.00 | 7.5 |
| | | 12.50 | 8.0 |
| | 24 | 100.00 | 7.0 |
| | | 50.00 | 6.5 |
| | | 25.00 | 5.0 |
| | | 12.50 | 5.0 |
| | 72 | 100.00 | 1.0 |
| | | 50.00 | 1.0 |
| | | 25.00 | 1.0 |
| | | 12.50 | 1.0 |
| Example 13 | −48 | 50.00 | 7.0 |
| | | 25.00 | 6.0 |
| | | 12.50 | 2.0 |
| | | 6.25 | 6.0 |
| | −24 | 50.00 | 7.0 |
| | | 25.00 | 5.0 |
| | | 12.50 | 5.0 |
| | | 6.25 | 1.0 |
| | 24 | 50.00 | 1.0 |
| | | 25.00 | 1.0 |
| | | 12.50 | 1.0 |
| | | 6.25 | 1.0 |
| Example 13 | 48 | 50.00 | 1.0 |
| | | 25.00 | 1.0 |
| | | 12.50 | 1.0 |
| | | 6.25 | 1.0 |
| Example 14 | −48 | 100.00 | 4.0 |
| | | 50.00 | 1.0 |
| | | 25.00 | 1.0 |
| | | 12.50 | 1.0 |
| | −24 | 100.00 | 1.0 |
| | | 50.00 | 1.0 |
| | | 25.00 | 1.0 |
| | | 12.50 | 1.0 |
| | 4 | 100.00 | 4.0 |
| | | 50.00 | 2.0 |
| | | 25.00 | 1.0 |
| | | 12.50 | 1.0 |
| | 48 | 100.00 | 4.0 |
| | | 50.00 | 1.0 |
| | | 25.00 | 1.0 |
| | | 12.50 | 1.0 |
| Example 15 | −72 | 100.00 | 7.0 |
| | | 50.00 | 7.0 |
| | | 25.00 | 6.0 |
| | | 12.50 | 2.0 |
| Example 15 | 72 | 100.00 | 1.0 |
| | | 50.00 | 1.0 |
| | | 25.00 | 1.0 |
| | | 12.50 | 1.0 |
| Example 16 | −72 | 100.00 | 1.0 |
| | | 100.00 | 6.5 |
| | | 50.00 | 1.0 |
| | | 50.00 | 6.5 |
| | | 25.00 | 1.0 |
| | | 25.00 | 1.0 |
| | | 12.50 | 1.0 |
| | | 12.50 | 1.0 |
| | 72 | 100.00 | 1.0 |
| | | 100.00 | 1.0 |
| | | 50.00 | 1.0 |
| | | 50.00 | 1.0 |
| | | 25.00 | 1.0 |
| Example 17 | −72 | 25.00 | 1.0 |
| | | 12.50 | 1.0 |
| | | 12.50 | 1.0 |
| | | 50.00 | 1.0 |
| | | 25.00 | 1.0 |
| | | 12.50 | 1.0 |
| | | 6.25 | 1.0 |
| | 72 | 50.00 | 1.0 |
| | | 25.00 | 1.0 |
| | | 12.50 | 1.0 |
| | | 6.25 | 1.0 |
| Example 18 | −72 | 100.00 | 5.0 |
| | | 50.00 | 4.0 |
| | | 25.00 | 5.0 |
| | | 12.50 | 5.0 |
| | 96 | 100.00 | 7.0 |
| | | 50.00 | 1.0 |
| | | 25.00 | 1.0 |
| | | 12.50 | 1.0 |

TEST 4

The compound of Example 1 was tested as a seed treatment against powdery mildew of wheat. Results are reported in Table 9. The rating scale is the 1–9 scale previously described.

TABLE 9

SEED TREATMENT
POWDERY MILDEW WHEAT

| Compound | Time in Hours | Rate G/KB | Disease Control Rating |
|---|---|---|---|
| Example 1 | 192 | 0.10 | 1.0 |
| | | | 1.0 |
| | | 1.00 | 5.0 |
| | | | 8.0 |

TESTS 5 to 13 & 13A

Tables 10 to 18A report the results of greenhouse tests of compounds of the invention against various fungal disease pathogens.

TABLE 10

FOLIAR APPLICATION
GRAPE DOWNY MILDEW

| Compound | Time in Hours | Rate in ppm | Disease Control Rating |
|---|---|---|---|
| Example 1 | −48 | 100.00 | 1.0 |
| | | 50.00 | 1.0 |
| | | 25.00 | 1.0 |
| | | 12.50 | 4.0 |
| | −24 | 100.00 | 1.0 |
| | | 50.00 | 1.0 |
| | | 25.00 | 1.0 |
| | | 12.50 | 1.0 |
| | 24 | 100.00 | 1.0 |
| | | 50.00 | 1.0 |
| | | 25.00 | 1.0 |
| | | 12.50 | 1.0 |
| | 48 | 100.00 | 1.0 |
| | | 50.00 | 1.0 |
| | | 25.00 | 1.0 |
| | | 12.50 | 1.0 |
| Example 4 | 4 | 400.00 | 8.0 |
| | | 100.00 | 1.0 |
| | | 50.00 | 1.0 |

TABLE 11

FOLIAR APPLICATION
GRAPE POWDERY MILDEW

| Compound | Time in Hours | Rate in ppm | Disease Control Rating |
|---|---|---|---|
| Example 1 | −73 | 100.00 | 9.0 |
|  |  | 50.00 | 9.0 |
|  |  | 25.00 | 3.0 |
|  | −72 | 100.00 | 7.0 |
|  |  | 50.00 | 8.0 |
|  |  | 25.00 | 7.0 |

TABLE 12

FOLIAR APPLICATION
APPLE POWDERY MILDEW

| Compound | Time in Hours | Rate in ppm | Disease Control Rating |
|---|---|---|---|
| Example 1 | 2 | 400.00 | 1.0 |
|  |  | 100.00 | 1.0 |
|  | 4 | 50.00 | 1.0 |
|  |  | 25.00 | 1.0 |
|  |  | 12.50 | 1.0 |
|  | 96 | 50.00 | 1.0 |
|  |  | 25.00 | 1.0 |
|  |  | 12.50 | 1.0 |

TABLE 13

FOLIAR APPLICATION
CUCURBIT POWDERY MILDEW

| Compound | Time in Hours | Rate in ppm | Disease Control Rating |
|---|---|---|---|
| Example 1 | 2 | 100.00 | 1.0 |
|  | 4 | 50.00 | 5.0 |
|  |  | 25.00 | 1.0 |
|  |  | 12.50 | 1.0 |
|  | 96 | 50.00 | 5.0 |
|  |  | 25.00 | 1.0 |
|  |  | 12.50 | 1.0 |

TABLE 14

FOLIAR APPLICATION
LEAF RUST OF WHEAT

| Compound | Time in Hours | Rate in ppm | Disease Control Rating |
|---|---|---|---|
| Example 1 | −72 | 50.00 | 1.0 |
|  |  | 25.00 | 1.0 |
|  |  |  | 1.0 |
|  |  | 12.50 | 1.0 |
|  |  |  | 1.0 |
|  |  | 6.12 | 1.0 |
|  | 2 | 400.00 | 1.0 |
|  |  | 100.00 | 1.0 |
|  |  | 25.00 | 1.0 |
|  | 72 | 25.00 | 1.0 |
|  |  | 12.50 | 1.0 |
|  |  | 6.12 | 1.0 |
|  | 92 | 50.00 | 1.0 |
|  |  | 25.00 | 1.0 |
|  |  | 12.50 | 1.0 |

TABLE 15

FOLIAR APPLICATION
RICE BLAST

| Compound | Time in Hours | Rate in ppm | Disease Control Rating |
|---|---|---|---|
| Example 1 | −72 | 200.00 | 1.0 |

TABLE 15-continued

FOLIAR APPLICATION
RICE BLAST

| Compound | Time in Hours | Rate in ppm | Disease Control Rating |
|---|---|---|---|
|  |  | 100.00 | 1.0 |
|  |  | 50.00 | 1.0 |
|  | −24 | 400.00 | 1.0 |
|  |  |  | 1.0 |
|  |  | 200.00 | 1.0 |
|  |  |  | 1.0 |
|  |  |  | 1.0 |
|  |  | 100.00 | 1.0 |
|  |  |  | 1.0 |
|  |  |  | 1.0 |
|  |  | 50.00 | 1.0 |
|  |  |  | 1.0 |
|  |  |  | 1.0 |
|  | 4 | 400.00 | 8.0 |
|  |  |  | 8.0 |
|  |  | 200.00 | 7.5 |
|  |  |  | 8.0 |
|  |  | 100.00 | 7.5 |
|  |  |  | 8.0 |
|  |  | 50.00 | 6.0 |
|  |  |  | 8.0 |
| Example 1 | 24 | 200.00 | 3.0 |
|  |  | 100.00 | 2.0 |
|  |  | 50.00 | 3.0 |
|  | 72 | 200.00 | 2.0 |
|  |  | 100.00 | 1.0 |
|  |  | 50.00 | 1.0 |
| Example 4 | −24 | 400.00 | 1.0 |
|  |  | 200.00 | 1.0 |
|  |  | 100.00 | 1.0 |
|  |  | 50.00 | 1.0 |
|  | 4 | 400.00 | 2.0 |
|  |  | 200.00 | 1.0 |
|  |  | 100.00 | 1.0 |
|  |  | 50.00 | 1.0 |
| Example 11 | −24 | 400.00 | 1.0 |
|  |  | 200.00 | 1.0 |
|  |  | 100.00 | 1.0 |
|  |  | 50.00 | 1.0 |
|  | 4 | 400.00 | 3.0 |
|  |  | 200.00 | 1.0 |
|  |  | 100.00 | 1.0 |
|  |  | 50.00 | 1.0 |
| Example 14 | −24 | 400.00 | 1.0 |
|  |  | 200.00 | 1.0 |
|  |  | 100.00 | 1.0 |
|  |  | 50.00 | 1.0 |
|  | 4 | 400.00 | 8.5 |
|  |  | 200.00 | 8.5 |
|  |  | 100.00 | 7.0 |
|  |  | 50.00 | 6.5 |
| Example 15 | −24 | 400.00 | 1.0 |
|  |  | 200.00 | 1.0 |
|  |  | 100.00 | 1.0 |
|  |  | 50.00 | 1.0 |
|  | 4 | 400.00 | 8.5 |
|  |  | 200.00 | 8.0 |
|  |  | 100.00 | 7.5 |
|  |  | 50.00 | 5.0 |
| Example 17 | −24 | 400.00 | 1.0 |
|  |  | 200.00 | 1.0 |
|  |  | 100.00 | 1.0 |
|  |  | 50.00 | 1.0 |
| Example 17 | 72 | 400.00 | 1.0 |
|  |  | 200.00 | 1.0 |
|  |  | 100.00 | 1.0 |
|  |  | 50.00 | 1.0 |

TABLE 16
SOIL DRENCH
RICE BLAST

| Compound | Time in Hours | Rate LB/A | Disease Control Rating |
|---|---|---|---|
| Example 1 | 48 | 10.00 | 1.0 |
| | | | 1.0 |
| | | 5.00 | 1.0 |
| | | | 1.0 |
| | | 2.50 | 1.0 |
| | | | 1.0 |
| Example 4 | 48 | 10.00 | 1.0 |
| | | 5.00 | 1.0 |
| | | 2.50 | 1.0 |
| Example 11 | 48 | 10.00 | 3.0 |
| | | 5.00 | 1.0 |
| | | 2.50 | 1.0 |
| Example 14 | 48 | 10.00 | 5.0 |
| | | 5.00 | 3.0 |
| | | 2.50 | 1.0 |
| Example 15 | 48 | 10.00 | 1.0 |
| | | 5.00 | 1.0 |
| | | 2.50 | 1.0 |

TABLE 17
FOLIAR APPLICATION
WHEAT SEPTORIA BLOTCH

| Compound | Time in Hours | Rate in ppm | Disease Control Rating |
|---|---|---|---|
| Example 1 | −72 | 6.25 | 1.0 |
| | | 3.12 | 1.0 |
| | 72 | 6.25 | 1.0 |
| | | 3.12 | 1.0 |

SEED TREATMENT
WHEAT SEPTORIA BLOTCH

| Compound | Time in Hours | Rate G/KG | Disease Control Rating |
|---|---|---|---|
| Example 1 | 192 | 1.00 | 1.0 |
| | | 0.10 | 1.0 |

TABLE 18A
FOLIAR APPLICATION
*PSEUDOCERCOSPORELLA HERPOTUCHOIDES*

| Compound | Time in Hours | Rate G/KG | Disease Control Rating |
|---|---|---|---|
| Example 1 | −504 | 400.00 | 2.0 |
| | −336 | 400.00 | 3.0 |
| | 4 | 400.00 | 7.0 |
| | | 100.00 | 2.0 |
| | | 25.00 | 1.0 |

FIELD TESTS

TEST 14

The compound of Example 1, formulated as a 1 lb per gallon emulsifiable concentrate, was evaluated against leaf rust (*Puccinia recondita tritici*), Septoria leaf blotch (*Septoria tritici*), and powdery mildew (*Erysiphe graminis tritici*) of wheat in field plots. Each test plot measured 5×10 ft, and three replicate plots per treatment were used. The spray compositions were prepared at concentrations required to provide the indicated application rates at an application volume of 63 gallons/acre. The compound was applied twice: at the boot stage (May 3) and at the early heading stage (May 14). The total rainfall between the first and second applications was 2.07 inches. The total rainfall in the first seven days following the second application was 1.41 inches. Disease control was rated 39 days after treatment (June 11). The results are given in Table 19. The rating scale used is 0–10, where 0 = no control and 10 = 100% control.

TABLE 19

| Rate (LB/A) | Disease Control Rating | | |
|---|---|---|---|
| | Leaf Rust | Leaf Blotch | Powdery Mildew |
| 0.25 | 0 | 0 | 9.6 |
| 0.5 | 3 | 3 | 9.8 |
| 1 | 3 | 4 | 9.8 |

TEST 15

A duplicate of Test 14 was simultaneously carried out on separate test plots in the same location. The results are given in Table 20. The rating scale is the 0–10 scale as described in Test 14.

TABLE 20

| Rate (LB/A) | Disease Control Rating | | |
|---|---|---|---|
| | Leaf Rust | Leaf Blotch | Powdery Mildew |
| 0.25 | 1.7 | 0 | 9.6 |
| 0.50 | 1.0 | 0 | 9.7 |
| 1.00 | 3.3 | 0 | 9.7 |

TEST 16

The compound of Example 1 was evaluated against powdery mildew (*Erysiphe graminis hordei*) of barley. Foliar application was used. Disease control was evaluated 7 and 14 days following application. Results are given in Table 21.

TABLE 21

| Application Rate (ppm) | Percent Disease Control | | |
|---|---|---|---|
| | Day 7 | Day 14 | |
| | 1st Leaf | 1st Leaf | 2nd Leaf |
| 1.56 | 20.6 | 19.3 | 42.6 |
| 6.25 | 100.0 | 69.5 | 54.4 |
| 25.00 | 100.0 | 98.0 | 85.6 |

TEST 17

The compound of Example 1 was evaluated against powdery mildew (*Erysiphe qraminis tritici*) of wheat. Application was foliar. Evaluations were made 7 and 14 days following application. Results are given in Table 22.

TABLE 22

| Application Rate (ppm) | Percent Disease Control | | |
|---|---|---|---|
| | Day 7 | Day 14 | |
| | 1st Leaf | 1st Leaf | 2nd Leaf |
| 1.56 | 60.3 | 58.5 | 47.6 |
| 6.25 | 100.0 | 89.6 | 79.2 |
| 25.00 | 100.0 | 91.8 | 86.1 |

TEST 18

The compound of Example 1 was evaluated for one, two and four day protectant activity against powdery mildew (*Erysiphe qraminis hordei*) of barley. Test plants were 8 to 10 cm tall, planted 12 to 14 specimens to a 7 cm pot. Three replicate pots were used for each treatment. Spray compositions were prepared at the indicated concentrations and were applied to run-off using a DeVilbis sprayer. For each application rate, one group of plants was treated one day before inoculation, another group was treated two days before inoculation, and a third group was treated four days before inoculation. Results are given in Table 23.

TABLE 23

| Treatment (days before inoculation) | Evaluation (days after application) | Appln Rate ppm | Percent Disease Control | |
|---|---|---|---|---|
| | | | 1st Leaf | 2nd Leaf |
| 1 | 8 | 1.56 | 68.5 | 32.0 |
| | | 6.25 | 100.0 | 66.0 |
| | | 25.00 | 100.0 | 66.0 |
| | 15 | 1.56 | 40.0 | 0 |
| | | 6.25 | 81.1 | 20.6 |
| | | 25.00 | 85.0 | 50.0 |
| 2 | 9 | 1.56 | 60.3 | 0 |
| | | 6.25 | 100.0 | 20.6 |
| | | 25.00 | 100.0 | 37.0 |
| | 16 | 1.56 | — | 37.5 |
| | | 6.25 | — | 29.76 |
| | | 25.00 | — | 18.75 |
| 4 | 11 | 1.56 | 60.3 | 14.3 |
| | | 6.25 | 68.5 | 14.3 |
| | | 25.00 | 96.7 | 14.3 |
| | 16 | 1.56 | 37.5 | — |
| | | 6.25 | 18.75 | — |
| | | 25.00 | 9.37 | — |
| | 18 | 1.56 | 14.3 | 7.4 |
| | | 6.25 | 78.6 | 7.4 |
| | | 25.00 | 96.4 | 70.8 |

TEST 19

Using the same procedure as in Test 18, the compound of Example 1 was evaluated for one, two and four day protectant activity against powdery mildew (*Erysiph graminis tritici*) of wheat. The results are given in Table 24.

TABLE 24

| Treatment (days before inoculation) | Evaluation (days after application) | Appln Rate (ppm) | Percent Disease Control | |
|---|---|---|---|---|
| | | | 1st Leaf | 2nd Leaf |
| 1 | 8 | 1.56 | 68.5 | — |
| | | 6.25 | 80.1 | — |
| | | 25.00 | 93.7 | — |
| | 15 | 1.56 | 26.5 | 20.6 |
| | | 6.25 | 63.3 | 37.0 |
| | | 25.00 | 76.8 | 37.0 |
| 2 | 9 | 1.56 | 37.0 | 0.0 |
| | | 6.25 | 84.3 | 37.0 |
| | | 25.00 | 84.3 | 60.3 |
| | 16 | 1.56 | 28.9 | 37.0 |
| | | 6.25 | 43.6 | 37.0 |
| | | 25.00 | 77.6 | 50.0 |
| 4 | 11 | 1.56 | 26.5 | 7.4 |
| | | 6.25 | 53.7 | 7.4 |
| | | 25.00 | 70.8 | 26.5 |
| | 18 | 1.56 | 37.0 | 0.0 |
| | | 6.25 | 0.0 | 0.0 |
| | | 25.00 | 50.0 | 20.6 |

TEST 20

The one, two and four curative activity of the compound of Example 1 was evaluated against powdery mildew (*Erysiphe graminis hordei*) of barley. The methods used were the same as in Test 18, except that the test compound was applied one, two or four days after inoculation, instead of before. Results are given in Table 25.

TABLE 25

| Treatment (days after inoculation) | Evaluation (days after application) | Appln Rate (ppm) | Percent Disease Control | |
|---|---|---|---|---|
| | | | 1st Leaf | 2nd Leaf |
| 1 | 6 | 1.56 | 20.6 | 14.3 |
| | | 6.25 | 84.3 | 73.0 |
| | | 25.00 | 100.0 | 82.0 |
| | 13 | 1.56 | 23.4 | 0.0 |
| | | 6.25 | 75.9 | 37.0 |
| | | 25.00 | 100.0 | 68.5 |
| 2 | 5 | 1.56 | 37.0 | 66.0 |
| | | 6.25 | 90.1 | 100.0 |
| | | 25.00 | 100.0 | 100.0 |
| | 12 | 1.56 | 20.6 | 14.3 |
| | | 6.25 | 80.1 | 78.6 |
| | | 25.00 | 100.0 | 83.0 |
| 4 | 3 | 1.56 | 60.3 | — |
| | | 6.25 | 68.5 | — |
| | | 25.00 | 80.1 | — |
| | 10 | 1.56 | 14.3 | 37.0 |
| | | 6.25 | 78.6 | 60.3 |
| | | 25.00 | 98.2 | 80.1 |

TEST 21

The one, two and four day curative activity of the compound of Example 1 was evaluated against powdery mildew (*Erysiphe graminis tritici*) of wheat using the same procedure as for Test 20. The results are reported in Table 26.

TABLE 26

| Treatment (days after inoculation) | Evaluation (days after application) | Appln Rate (ppm) | Percent Disease Control | |
|---|---|---|---|---|
| | | | 1st Leaf | 2nd Leaf |
| 1 | 6 | 1.56 | 50.0 | 71.4 |
| | | 6.25 | 100.0 | 100.0 |
| | | 25.00 | 100.0 | 100.0 |
| | 13 | 1.56 | 42.5 | 7.4 |
| | | 6.25 | 96.4 | 53.7 |
| | | 25.00 | 100.0 | 84.6 |
| 2 | 5 | 1.56 | 93.7 | — |
| | | 6.25 | 100.0 | — |
| | | 25.00 | 100.0 | — |
| | 12 | 1.56 | 52.4 | 7.4 |
| | | 6.25 | 98.7 | 53.7 |
| | | 25.00 | 98.7 | 53.7 |
| 4 | 3 | 1.56 | 66.0 | — |
| | | 6.25 | 83.0 | — |
| | | 25.00 | 100.0 | — |
| | 10 | 1.56 | 70.8 | 54.6 |
| | | 6.25 | 100.0 | 77.3 |
| | | 25.00 | 100.0 | 100.0 |

TEST 22

The eradicant activity of the compound of Example 1 was evaluated against powdery mildew (*Erysiphe graminis hordei*) of barley. The methods used were the same as in Test 18, except that the test compound was applied five days after inoculation. Results are given in Table 27.

TABLE 27

| Evaluation (days after application) | Application Rate (ppm) | Percent Disease Control | |
|---|---|---|---|
| | | 1st Leaf | 2nd Leaf |
| 2 | 6.25 | 41.7 | — |
| | 25.00 | 63.3 | — |
| | 50.00 | 70.8 | — |

TABLE 27-continued

| Evaluation (days after application) | Application Rate (ppm) | Percent Disease Control | |
|---|---|---|---|
| | | 1st Leaf | 2nd Leaf |
| 9 | 6.25 | 76.2 | 83.0 |
| | 25.00 | 85.0 | 73.0 |
| | 50.00 | 92.5 | 89.3 |

TEST 23

The eradicant activity of the compound of Example 1 was evaluated against powdery mildew of barley using the same procedure as in Test 18, except that the compound was applied six days after inoculation. Results were evaluated eight days after application. Results are given in Table 28.

TABLE 28

| Application Rate (ppm) | Percent Disease Control | |
|---|---|---|
| | 1st Leaf | 2nd Leaf |
| 6.25 | 73.5 | 88.0 |
| 25.00 | 58.0 | 90.4 |
| 50.00 | 47.1 | 90.4 |

TEST 24

The eradicant activity of the compound of Example 1 was evaluated against powdery mildew (*Erysiphe graminis tritici*) of wheat. The procedure used was the same as in Test 19, except the compound was applied five days after inoculation. Results are given in Table 29.

TABLE 29

| Evaluation (days after application) | Appln Rate (ppm) | Percent Disease Control | |
|---|---|---|---|
| | | 1st Leaf | 2nd Leaf |
| 2 | 6.25 | 60.3 | — |
| | 25.00 | 60.3 | — |
| | 50.00 | 68.5 | — |
| 9 | 6.25 | 93.0 | — |
| | 25.00 | 93.0 | — |
| | 50.00 | 100.0 | — |

TEST 25

The eradicant activity of the compound of Example 1 against powdery mildew of wheat was evaluated using the procedure of Test 19, except the compound was applied six days after inoculation. Results were evaluated after eight days, and are given in Table 30.

TABLE 30

| Application Rate (ppm) | Percent Disease Control 1st Leaf |
|---|---|
| 6.25 | 81.6 |
| 25.00 | 70.8 |
| 50.00 | 76.8 |

TEST 26

The two day protectant activity of the compound of Example 1 against powdery mildew (*Erysiphe graminis hordei*) of barley was evaluated using the procedure of Test 18, except the compound was applied two days before inoculation of the plants. Results are given in Table 31.

TABLE 31

| Evaluation (days after application) | Appln Rate (ppm) | Percent Disease Control | |
|---|---|---|---|
| | | 1st Leaf | 2nd Leaf |
| 9 | 0.78 | 29.3 | 20.6 |
| | 1.56 | 43.9 | 20.6 |
| | 3.12 | 71.9 | 37.0 |
| | 6.25 | 95.3 | 60.3 |
| 16 | 0.78 | 8.9 | 12.5 |
| | 1.56 | 8.9 | 12.5 |
| | 3.12 | 35.2 | 21.6 |
| | 6.25 | 74.3 | 50.6 |

TEST 27

The two day protectant activity of the compound of Example 1 against powdery mildew of wheat was evaluated using the procedure of Test 19, except that the compound was applied two days before inoculation of the plants. Results are given in Table 32.

TABLE 32

| Evaluation (days after application) | Appln Rate (ppm) | Percent Disease Control | |
|---|---|---|---|
| | | 1st Leaf | 2nd Leaf |
| 9 | 0.78 | 0.0 | 0.0 |
| | 1.56 | 10.9 | 0.0 |
| | 3.12 | 29.3 | 0.0 |
| | 6.25 | 77.7 | 25.1 |
| 16 | 0.78 | 62.5 | 0.0 |
| | 1.56 | 52.75 | 20.6 |
| | 3.12 | 37.50 | 20.6 |
| | 6.25 | 14.88 | 37.0 |

TEST 28

The two day curative activity of the compound of Example 1 against powdery mildew of barley was evaluated using the procedure of Test 18, except the compound was applied two days following inoculation of the test plants with *Erysiphe graminis hordei*. Test results are reported in Table 33.

TABLE 33

| Evaluation (days after application) | Appln Rate (ppm) | Percent Disease Control | |
|---|---|---|---|
| | | 1st Leaf | 2nd Leaf |
| 5 | 0.78 | 62.5 | 37.0 |
| | 1.56 | 62.5 | 37.0 |
| | 3.12 | 52.8 | 50.0 |
| | 6.25 | 98.0 | 100.0 |
| 12 | 0.78 | 32.7 | 10.9 |
| | 1.56 | 57.6 | 29.3 |
| | 3.12 | 46.6 | 10.9 |
| | 6.25 | 91.6 | 55.4 |

TEST 29

The two day curative activity of the compound of Example 1 against powdery mildew of wheat was evaluated using the procedure of Test 19, except the compound was applied two days following inoculation of the test plants with *Erysiphe graminis tritici*. Test results are given in Table 34.

TABLE 34

| Evaluation (days after application) | Appln Rate (ppm) | Percent Disease Control | |
|---|---|---|---|
| | | 1st Leaf | 2nd Leaf |
| 5 | 0.78 | 57.9 | 40.5 |
| | 1.56 | 79.0 | 80.2 |
| | 3.12 | 100.0 | 100.0 |
| | 6.25 | 100.0 | 100.0 |
| 12 | 0.78 | 40.5 | — |
| | 1.56 | 62.5 | — |
| | 3.12 | 92.6 | — |
| | 6.25 | 95.3 | — |

Combinations

Fungal disease pathogens are known to develop resistance to fungicides. When strains resistant to a fungicide do develop, it becomes necessary to apply larger and larger amounts of the fungicide to obtain desired results. To retard the development of resistance to new fungicides, it is desirable to apply the new fungicides in combination with other fungicides. Use of a combination product also permits the product's spectrum of activity to be adjusted.

Accordingly, another aspect of the invention is a fungicidal combination comprising at least 1% by weight of a compound of formula (I) in combination with a second fungicide.

Contemplated classes of fungicides from which the second fungicide may be selected include:

(1) N-substituted azoles, for example propiconazole, triademefon, flusilazol, diniconazole, ethyltrianol, myclobutanil, and prochloraz;

(2) pyrimidines, such as fenarimol and nuarimol;

(3) morpholines, such as fenpropimorph and tridemorph;

(4) piperazines, such as triforine; and (5) pyridines, such as pyrifenox. Fungicides in these five classes all function by inhibiting sterol biosynthesis. Additional classes of contemplated fungicides, which have other mechanisms of action, include:

(6) dithiocarbamates, such as maneb and mancozeb;

(7) phthalimides, such as captafol;

(8) isophthalonitriles, such as chlorothalonil;

(9) dicarboximides, such as iprodione;

(10) benzimidazoles, such as benomyl and carbendazim;

(11) 2-aminopyrimidines, such as ethirimol;

(12) carboxamides, such as carboxin; and

(13) dinitrophenols, such as dinocap.

The fungicide combinations of the invention contain at least 1%, ordinarily 20 to 80%, and more typically 50 to 75% by weight of a compound of formula (I).

Certain combinations within the invention have been found to provide synergistic activity against a number of fungal pathogens. Synergism against powdery mildew and rust has been observed not only in greenhouse tests, but also under field conditions.

More specifically, synergism has been observed for certain combinations in which the second fungicide component was nuarimol, benomyl, chlorothalonil, prochloraz, propiconazole, triademefon, or tridemorph, as evident in the following greenhouse and field test data. In general, it is believed that synergism can be expected under appropriate conditions from combinations comprising a compound of the formula (I) in combination with a sterol inhibiting fungicide of the type that inhibits C-14 demethylation; but, as evidenced by the foregoing list, synergism has also been observed with other classes of fungicides.

When it is stated that a composition displays synergism, we mean that the percent control of disease observed in a test of the composition exceeds the value predicted by the equation $$E = X + Y - \frac{XY}{100}$$

where X is the percent control observed in a test of component A applied at rate p, y is the percent control observed in a test of component B applied at rate q, and E is the expected percent control for the combination of A +B applied at rate p +q. This test is based on an article by S. R. Colby, "Calculating Synergistic and Antagonistic Responses of Herbicide Combinations" Weeds, vol. 15, 20–22 (1967). The test operates on the theory that if component A kills 50% of disease organisms, then the best B can be expected to do is kill 50% of the remaining organisms, for an expected total of 75% control.

A given fungicidal composition may display synergism under certain conditions and not under others. Factors significant in determining whether synergism is displayed include, for example, the application rate, the timing of the application, and the genetic resistance of disease organisms to one or the other of the components of the composition. When a combination is applied at a rate such that the applied amount of one component alone would afford substantially complete control of the organism, there is little room for improvement, and the synergistic potential of the combination may not be apparent. In regard to timing, if an application of fungicide is made before the fungal disease organism is well established, the organism is more susceptible, and there is less opportunity to show synergistic potential than in the case where the disease organism is well established. On the other hand, if a disease organism is genetically resistant to one component of a combination, so that the applied amount of the one component alone would afford little control of that particular organism, there is more opportunity for the combination to show synergism against that organism than in a case where a similar application rate is used against a non-resistant disease organism.

Combination Tests

Greenhouse Tests

TEST 30

In this test, the compound of Example 1 was foliar applied in combination with one of several known compounds to wheat that was infected with powdery mildew. To test eradicant activity, wheat plants in one group were inoculated with disease organism 72 hours before treatment (−72 hours). To test protectant activity, wheat plants in another group were treated 72 hours before inoculation (+72 hours). The results, using the previously described 1–9 scale, were as follows.

| | Powdery Mildew | | |
|---|---|---|---|
| | Application Rate | Disease Control Rating | |
| Composition | (ppm) | (−72 hr) | (+72 hr) |
| Example 1 | 6.25 | 4.0 | 3.0 |
| | 12.50 | 5.0 | 3.0 |
| | 25.00 | 7.0 | 3.0 |

-continued

| Composition | Powdery Mildew Application Rate (ppm) | Disease Control Rating (−72 hr) | (+72 hr) |
|---|---|---|---|
| Example 1/prochloraz | 3.12/1.56 | 5.0 | 3.0 |
| | 6.25/3.12 | 5.0 | 3.0 |
| | 12.50/6.25 | 8.5 | 3.0 |
| Example 1/nuarimol | 3.12/1.56 | 7.0 | 6.0 |
| | 6.25/3.12 | 8.0 | 7.0 |
| | 12.50/6.25 | 9.0 | 7.0 |
| Example 1/propiconazole | 3.12/1.56 | 5.0 | 3.0 |
| | 6.25/3.12 | 7.5 | 3.0 |
| | 12.50/6.25 | 7.5 | 4.5 |
| Example 1/triademefon | 3.12/6.25 | 3.0 | 3.0 |
| | 6.25/12.50 | 5.0 | 5.0 |
| | 12.50/25.00 | 6.5 | 7.5 |
| Example 1/tridemorph | 3.12/6.25 | 3.0 | 3.0 |
| | 6.25/12.50 | 4.5 | 3.0 |
| | 12.50/25.00 | 6.0 | 3.0 |
| prochloraz | 1.56 | 4.0 | 3.0 |
| | 3.12 | 7.0 | 3.0 |
| nuarimol | 1.56 | 2.0 | 3.0 |
| | 3.12 | 4.0 | 3.0 |
| propiconazole | 1.56 | 5.0 | 5.0 |
| | 3.12 | 4.0 | 5.0 |
| triademefon | 6.25 | 4.0 | 5.0 |
| | 12.50 | 5.0 | 7.0 |
| tridemorph | 6.25 | 3.0 | 3.0 |
| | 12.50 | 3.0 | 3.0 |

TEST 31

In this test the compound of Example 1 was again foliar applied in combination with one of several known compounds, to wheat infected with powdery mildew. Eradicant activity was tested by inoculating a group of wheat plants with disease organism 72 hours before treatment (−72 hours). Protectant activity was tested by inoculating another group of wheat plants 72 hours after treatment (+72 hours). The results, using the previously described 1-9 rating scale, were as follows:

| Composition | Powdery Mildew Application Rate (ppm) | Disease Control Rating (−72 hr) | (+72 hr) |
|---|---|---|---|
| Example 1 | 3.12 | 5.5 | 1.0 |
| | 6.25 | 7.5 | 1.0 |
| Example 1/benomyl | 3.12/3.12 | 9.0 | 1.0 |
| | 6.25/6.25 | 9.0 | 1.0 |
| | 12.5/12.5 | 9.0 | 1.0 |
| Example 1/chlorothalonil | 3.12/12.5 | 9.0 | 1.0 |
| | 6.25/25.0 | 9.0 | 1.0 |
| | 12.50/50.0 | 9.0 | 1.0 |
| Example 1/nuarimol | 3.12/3.12 | 9.0 | 1.0 |
| | 6.25/6.25 | 9.0 | 1.0 |
| | 12.50/12.50 | 9.0 | 1.0 |
| Example 1/propiconazole | 3.12/3.12 | 9.0 | 1.0 |
| | 6.25/6.25 | 9.0 | 1.0 |
| | 12.50/12.50 | 9.0 | 3.0 |
| Example 1/triademefon | 3.12/6.25 | 9.0 | 1.0 |
| | 6.25/12.50 | 9.0 | 5.0 |
| | 12.50/25.0 | 9.0 | 5.0 |
| benomyl | 3.12 | 7.5 | 1.0 |
| | 6.25 | 8.5 | 1.0 |
| | 12.50 | 9.0 | 1.0 |
| chlorothalonil | 12.5 | 1.0 | 1.0 |
| | 25.0 | 1.0 | 1.0 |
| nuarimol | 3.12 | 8.0 | 1.0 |
| | 6.25 | 9.0 | 3.0 |
| propiconazole | 3.12 | 9.0 | 1.0 |
| | 6.25 | 9.0 | 2.0 |
| triademefon | 12.5 | 8.0 | 5.0 |
| | 25.0 | 9.0 | 5.0 |

TEST 32

In this test the compound of Example 1 was again foliar applied in combination with one of several known compounds, to wheat infected with powdery mildew. Eradicant activity was tested by inoculating a group of wheat plants with disease organism 50 hours before treatment (−50 hours). Protectant activity was tested by inoculating another group of wheat plants 24 hours after treatment (+24 hours). The results, using the previously described 1-9 scale, were as follows:

| Composition | Powdery Mildew Application Rate (ppm) | Disease Control Rating (−50 hr) | (+24 hr) |
|---|---|---|---|
| Example 1 | 3.12 | 3.0 | 5.0 |
| | 6.25 | 5.0 | 5.0 |
| Example 1/benomyl | 1.56/1.56 | 9.0 | 5.0 |
| | 1.56/3.12 | 8.0 | 8.5 |
| | 3.12/1.56 | 9.0 | 5.0 |
| Example 1/chlorothalonil | 1.56/6.25 | 3.0 | 5.0 |
| | 1.56/12.5 | 3.0 | 5.0 |
| | 3.12/6.25 | 5.0 | 7.0 |
| | 3.12/12.5 | 8.5 | 7.0 |
| | 6.25/6.25 | 9.0 | 7.0 |
| | 6.25/12.5 | 9.0 | 7.0 |
| Example 1/propiconazole | 1.56/1.56 | 9.0 | 6.5 |
| | 3.12/1.56 | 9.0 | 9.0 |
| | 6.25/1.56 | 9.0 | 9.0 |
| Example 1/nuarimol | 1.56/1.56 | 9.0 | 9.0 |
| | 3.12/1.56 | 8.8 | 9.0 |
| | 3.12/3.12 | 9.0 | 9.0 |
| benomyl | 1.56 | 5.0 | 5.0 |
| | 3.12 | 8.0 | 6.0 |
| chlorothalonil | 12.5 | 1.0 | 1.0 |
| | 25.0 | 1.0 | 1.0 |
| propiconazole | 1.56 | 7.0 | 9.0 |
| | 3.12 | 7.0 | 9.0 |
| nuarimol | 1.56 | 6.0 | 7.0 |
| | 3.12 | 8.0 | 7.0 |

TEST 33

In this test the compound of Example 1 was foliar applied in combination with one of several known compounds, to wheat plants infected with powdery mildew and to wheat plants infected with leaf rust. Eradicant (−72 hr) and protectant (+72 hr) activity were determined. The results, using the previously described 1-9 scale, were as follows:

| Composition | Leaf Rust Application Rate (ppm) | Disease Control Rating (−72 hr) | (+72 hr) |
|---|---|---|---|
| Example 1 | 6.12 | 1.0 | 1.0 |
| | 12.50 | 1.0 | 1.0 |
| | 25.0 | 1.0 | 1.0 |
| Example 1/nuarimol | 3.12/3.12 | 3.0 | 3.0 |
| | 6.25/6.25 | 5.0 | 3.0 |
| | 12.5/12.5 | 9.0 | 5.0 |
| Example 1/prochloraz | 3.12/3.12 | 1.0 | 1.0 |
| | 6.25/6.25 | 1.0 | 1.0 |
| | 12.5/12.5 | 1.0 | 1.0 |
| Example 1/propiconazole | 3.12/3.12 | 9.0 | 3.0 |
| | 6.25/6.25 | 9.0 | 5.0 |
| | 12.5/12.5 | 9.0 | 7.0 |
| Example 1/triademefon | 3.12/3.12 | 4.0 | 1.0 |
| | 6.25/6.25 | 4.0 | 1.0 |
| | 12.5/12.5 | 4.5 | 1.0 |
| Example 1/tridemorph | 3.12/3.12 | 1.0 | 1.0 |
| | 6.25/6.25 | 1.0 | 1.0 |
| | 12.5/12.5 | 1.0 | 1.0 |

-continued

| Composition | | | |
|---|---|---|---|
| nuarimol | 12.5 | 9.0 | 3.0 |
| prochloraz | 12.5 | 1.0 | 9.5 |
| propiconazole | 12.5 | 9.0 | 4.0 |
| triademefon | 12.5 | 4.0 | 1.0 |
| tridemorph | 12.5 | 1.0 | 1.0 |

| | Powdery Mildew | | |
|---|---|---|---|
| | Application Rate | Disease Control Rating | |
| Composition | (ppm) | (−72 hr) | (+72 hr) |
| Example 1 | 12.5 | 67 | 49.5 |
| Example 1/nuarimol | 3.12/3.12 | 8.5 | 4.0 |
| | 6.25/6.25 | 9.0 | 7.0 |
| | 12.5/12.5 | 9.0 | 8.0 |
| Example 1/prochloraz | 3.12/3.12 | 6.0 | 4.0 |
| | 6.25/6.25 | 7.0 | 4.0 |
| | 12.5/12.5 | 8.5 | 5.0 |
| Example 1/propiconazole | 3.12/3.12 | 7.0 | 4.0 |
| | 6.25/6.25 | 7.0 | 6.0 |
| | 12.5/12.5 | 8.0 | 8.5 |
| Example 1/triademefon | 3.12/3.12 | 3.0 | 4.0 |
| | 6.25/6.25 | 4.0 | 4.0 |
| | 12.5/12.5 | 5.0 | 5.0 |
| Example 1/tridemorph | 3.12/3.12 | 3.0 | 5.0 |
| | 6.25/6.25 | 4.0 | 5.0 |
| | 12.5/12.5 | 5.0 | 6.0 |
| nuarimol | 12.5 | 5.0 | 4.0 |
| prochloraz | 12.5 | 5.0 | 4.0 |
| propiconazole | 12.5 | 5.0 | 4.0 |
| triademefon | 12.5 | 5.0 | 3.0 |
| tridemorph | 12.5 | 6.0 | 1.0 |

TEST 34

In this test the compound of Example 1 was foliar applied in combination with one of several known compounds, to wheat infected with leaf rust. Eradicant (−72 hr) and protectant (+92 hr) activities were determined. The results, using the previously described 1-9 scale, were as follows:

| | Leaf Rust | | |
|---|---|---|---|
| | Application Rate | Disease Control Rating | |
| Composition | (ppm) | (−72 hr) | (+92 hr) |
| Example 1 | 25 | 1.0 | 1.0 |
| Example 1/nuarimol | 6.25/6.25 | 4.0 | 1.0 |
| | 12.5/12.5 | 9.0 | 1.0 |
| | 25.0/25.0 | 9.0 | 1.0 |
| Example 1/prochloraz | 6.25/6.25 | 1.0 | 1.0 |
| | 12.5/12.5 | 1.0 | 1.0 |
| | 25.0/25.0 | 1.0 | 1.0 |
| Example 1/propiconazole | 6.25/6.25 | 9.0 | 6.0 |
| | 12.5/12.5 | 9.0 | 7.0 |
| | 25.0/25.0 | 9.0 | 7.0 |
| Example 1/triademefon | 6.25/6.25 | 4.0 | 1.0 |
| | 12.5/12.5 | 4.0 | 1.0 |
| | 25.0/25.0 | 5.5 | 4.0 |
| Example 1/tridemorph | 6.25/6.25 | 1.0 | 1.0 |
| | 12.5/12.5 | 1.0 | 1.0 |
| | 25.0/25.0 | 1.0 | 1.0 |
| nuarimol | 25.0 | 9.0 | 1.0 |
| prochloraz | 25.0 | 1.0 | 1.0 |
| propiconazole | 25.0 | 9.0 | 6.0 |
| triademefon | 25.0 | 7.0 | 3.0 |
| tridemorph | 25.0 | 1.0 | 1.0 |

TEST 35

In this test the compound of Example 1 was foliar applied in combination with one of several known compounds, to wheat infected with Septoria leaf blotch. Eradicant (−72 hr) and protectant (+72 hr) activities were determined. The results, using the previously described 1-9 scale, were as follows:

| | Septoria Leaf Blotch | | |
|---|---|---|---|
| | Application Rate | Disease Control Rating | |
| Composition | (ppm) | (−72 hr) | (+72 hr) |
| Example 1 | 3.12 | 1.0 | 1.0 |
| | 6.25 | 1.0 | 1.0 |
| Example 1/benomyl | 1.56/1.56 | 5.0 | 6.5 |
| | 1.56/3.12 | 8.0 | 7.0 |
| | 3.12/1.56 | 5.0 | 7.0 |
| Example 1/chlorothalonil | 1.56/6.25 | 3.0 | 6.0 |
| | 1.56/12.50 | 3.0 | 6.0 |
| | 3.12/6.25 | 3.0 | 7.0 |
| | 3.12/12.50 | 3.0 | 7.0 |
| | 6.25/6.25 | 3.0 | 7.0 |
| | 6.25/12.50 | 5.0 | 6.5 |
| Example 1/nuarimol | 1.56/1.56 | 3.0 | 3.5 |
| | 3.12/1.56 | 5.0 | 6.0 |
| | 3.12/3.12 | 7.0 | 6.0 |
| Example 1/propiconazole | 1.56/1.56 | 8.0 | 6.5 |
| | 3.12/1.56 | 9.0 | 5.0 |
| | 6.25/1.56 | 3.0 | 5.0 |
| benomyl | 1.56 | 5.0 | 1.0 |
| chlorothalonil | 12.5 | 4.0 | 5.0 |
| nuarimol | 1.56 | 4.0 | 1.0 |
| | 3.12 | 7.0 | 4.0 |
| propiconazole | 1.56 | 9.0 | 1.0 |

FIELD TESTS

TEST 36

Barley

Field studies were carried out in England and in France wherein the compound of Example 1 was applied alone and in combination with one of two known compounds to barley that was infected with powdery mildew (*Erysiphe graminis hordei*). Results were as follows:

| | Application Rate | Observed % Disease Control | |
|---|---|---|---|
| Composition | (g/HA) | England* | France** |
| Example 1 | 56 | 26 | 69 |
| | 112 | 64 | 62 |
| propiconazole | 56 | 50 | 89 |
| | 112 | 87 | 91 |
| chlorothalonil | 1100 | 16 | 37 |
| Example 1/ propiconazole | 56/56 | 79 | 91 |
| | 112/112 | 89 | 95 |
| Example 1/ chlorothalonil | 56/1100 | 58 | 74 |
| | 112/1100 | 50 | 69 |

*untreated control had 74% disease
**untreated control had 25% disease

TEST 37

Wheat

Field Studies were carried out in the U.S. wherein the compound of Example 1 was applied alone and in combination with propiconazole to wheat (Hart, Monon) that was infected with powdery mildew (*Erisphe graminis tritici*). Results were as follows:

| Composition | Application Rate (g/HA) | Observed % Disease Control* |
|---|---|---|
| Example 1 | 56 | 88 |
| | 112 | 91 |
| propiconazole | 56 | 72 |

| Composition | Application Rate (g/HA) | Observed % Disease Control* |
|---|---|---|
| | 112 | 91 |
| Example 1/ | 56/56 | 97 |
| propiconazole | 112/112 | 98 |

*untreated control had 66% disease

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide adducts of alkyl phenols.

Emulsifiable concentrates of the compounds comprise a convenient concentration of a compound, such as from about 10% to about 50% by weight of liquid, dissolved in an inert carrier which is a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from the same types of surfactants discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

The following formulations of compounds of the invention have been prepared, and are typical of compositions useful in the practice of the present invention.

| A. Emulsifiable Concentrate | |
|---|---|
| Compound of Example 1 | 7.8% |
| propiconazole | 7.8 |
| "Stepan 551-85" | 10.0 |
| (nonionic/anionic surfactant blend) | |
| cyclohexanone | 25.0 |
| "Exxon 200" (naphthalenic solvent) | 49.4 |
| | 100.0 |
| B. Emulsifiable Concentrate | |
| Compound of Example 1 | 7.8% |
| propiconazole | 7.8 |
| "Stepan 551-85" | 3.0 |
| cyclohexanone | 32.0 |
| "Exxon 200" | 49.4 |
| | 100.0 |
| C. Emulsifiable Concentrate | |
| Compound of Example 1 | 12.50% |
| "Toximul D" | 1.25 |
| (nonionic/anionic surfactant blend) | |
| "Toximul H" | 3.75 |
| (nonionic/anionic surfactant blend) | |
| "Panosol AN3N" | 72.50 |
| (naphthalenic solvent) | |
| "Dowanol PM" | 10.00 |
| (propylene glycol monomethyl ether) | |
| | 100.00 |
| D. Emulsifiable Concentrate | |
| Compound of Example 1 | 12.50% |
| "Toximul H" | 10.00 |
| "Panosol AN3N" | 67.50 |
| "Dowanol PM" | 10.00 |
| | 100.00 |
| E. Aqueous Suspension | |
| Compound of Example 1 | 47.00% |
| "Pluronic L-122" | 2.00 |
| (ethylene oxide/propylene oxide block co-polymer) | |
| "AF-100" | 0.25 |
| (silicon based antifoam agent) | |
| xanthan gum | 0.05 |

| -continued | |
|---|---|
| veegum | 0.25 |
| propylene glycol | 6.00 |
| "Dowicil 75" | 0.20 |
| (biocide/preservative) | |
| water | 44.25 |
| | 100.00 |
| F. Aqueous Suspension | |
| Compound of Example 1 | 47.00% |
| "Pluronic L-122" | 2.00 |
| "Reax 88B" | 1.00 |
| (lignosulfonate dispersing agent) | |
| "AF-100" | 0.25 |
| xanthan gum | 0.05 |
| veegum | 0.25 |
| propylene glycol | 6.00 |
| "Dowicil 75" | 0.20 |
| water | 43.25 |
| | 100.00 |
| G. Aqueous Suspension | |
| Compound of Example 1 | 47.00% |
| "Pluronic L-122" | 2.00 |
| "Gafac RE-610" (anionic surfactant) | 2.00 |
| "AF-100" | 0.25 |
| xanthan gum | 0.05 |
| veegum | 0.25 |
| propylene glycol | 6.00 |
| "Dowicil 75" | 0.20 |
| water | 42.25 |
| | 100.00 |
| H. Aqueous Suspension | |
| Compound of Example 1 | 12.20% |
| "Makon 10" | 1.00 |
| (10 moles ethyleneoxide nonyl phenol surfactant) | |
| "Polyfon H" | 0.50 |
| (lignosulfonate dispersing agent) | |
| "AF-100" | 0.20 |
| propylene glycol | 10.00 |
| "Proxel-GXL" | 0.05 |
| (biocide/preservative) | |
| veegum | 0.88 |
| xanthan gum | 0.22 |
| water | 74.95 |
| | 100.00 |
| I. Aqueous Suspension | |
| Compound of Example 1 | 12.20% |
| "Makon 10" | 1.00 |
| "Polyfon H" | 0.50 |
| "AF-100" | 0.20 |
| "Proxel-GXL" | 0.05 |
| propylene glycol | 10.00 |
| veegum | 0.80 |
| xanthan gum | 0.20 |
| water | 75.05 |
| | 100.00 |
| J. Aqueous Suspension | |
| Compound of Example 1 | 12.10% |
| "Makon 10" | 1.00 |
| "Polyfon H" | 0.50 |
| "AF-100" | 0.20 |
| "Proxel GXL" | 0.05 |
| propylene glycol | 10.00 |
| veegum | 1.44 |
| xanthan gum | 0.36 |
| water | 74.35 |
| | 100.00 |
| K. Aqueous Suspension | |
| Compound of Example 1 | 47.00% |
| "AF-100" | 0.25 |
| "Makon 10" | 2.00 |
| "Polyfon H" | 2.00 |
| xanthan gum | 0.05 |
| propylene glycol | 6.00 |
| veegum | 0.25 |
| "Dowicil 75" | 0.20 |
| water | 42.25 |
| | 100.00 |
| L. Aqueous Suspension | |
| Compound of Example 1 | 47.00% |

| -continued | |
|---|---|
| "Sponto AD6-29" | 2.00 |
| (nonionic/anionic blend) | |
| "Polyfon H" | 1.00 |
| "AF-100" | 0.25 |
| "Dowicil 75" | 0.20 |
| xanthan gum | 0.05 |
| propylene glycol | 6.00 |
| veegum | 0.25 |
| water | 43.25 |
| | 100.00 |
| M. Wettable Powder | |
| Compound of Example 1 | 52.08% |
| "Stepanol ME" | 4.00 |
| (sodium lauryl sulfate) | |
| "Hi Sil 233" (silica carrier) | 5.00 |
| "Polyfon H" | 4.00 |
| Barden clay | 34.92 |
| | 100.00 |

We claim:

1. A compound of the formula (I):

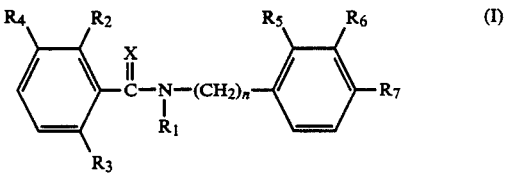

wherein:
X=O, S, or NOH;
$R^1$ is H or $CH_3$;
n=1, 2, or 3;
$R^2$, $R^3$, and $R^4$ are as defined in one of the following paragraphs
(a) $R^2$ and $R^3$ are independently Cl or Br, and $R^4$ is H;
(b) $R^2$, $R^3$ and $R^4$ are independently Cl or Br;
(c) $R^2$ is F, $R^3$ is Cl, and $R^4$ is H; or
(d) $R^2$ and $R^3$ are $CH_3$ or $C_2H_5$, and $R^4$ is H; and
one or $R^6$ and $R^7$ is $CF_3$, $R^5$ and the other and $R^6$ and $R^7$ is H.

2. A compound of the formula (Ia)

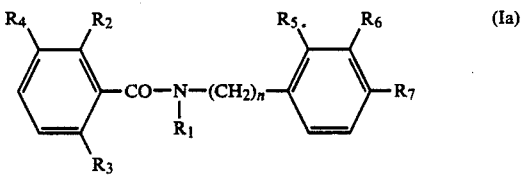

wherein:
$R^1$ is H or $CH_3$;
n=1, 2, or 3;
$R^2$, $R^3$, and $R^4$ are as defined in one of the following paragraphs
(a) $R^2$ and $R^3$ are Cl, and $R^4$ is H;
(b) $R^2$, $R^3$ $R^3$ and $R^4$ are Cl; or
(c) $R^2$ is F, $R^3$ is Cl, and $R^4$ is H; and
one of $R^6$ and $R^7$ is $CF_3$, $R^5$ and the other of $R^6$ and $R^7$ is H.

3. A compound of claim 2 wherein $R^2$ and $R^3$ are both Cl.

4. A compound of claim 3 wherein $R^1$ is H.

5. The compound of claim 17 which is 2,6-dichloro-N-[[4-(trifluoromethyl)phenyl]methyl]benzamide.

6. The compound of claim 17 which is 2,6-dichloro-N-[[3-(trifluoromethyl)phenyl]methyl]benzamide.

7. The compound of claim 4 which is 2,6,-dichloro-N-[3-[4-(trifluoromethyl)phenyl]propyl]benzamide.

8. The compound of claim 4 which is 2,6,-dichloro-N-[2-[3-(trifluoromethyl)phenyl]ethyl]benzamide.

9. The compound of claim 4 which is 2,6,-dichloro-N-methyl-N-[[4-trifluoromethyl)phenyl]methyl]benzamide.

10. A compound of claim 2 wherein $R^1$ is H.

11. The compound of claim 10 which is 2-chloro-6-fluoro-N-[[4-(trifluoromethyl)phenyl]methyl]benzamide.

12. The compound of claim 10 which is 2,3,6-trichloro-N-[[4-trifluoromethyl)phenyl]methyl]benzamide.

13. The compound of claim 10 which is 2,3,6-trichloro-N-[[3-(trifluoromethyl)phenyl]methyl]benzamide.

14. A fungicidal composition comprising at least 1% by weight of a compound of claim 2 in combination with a second plant fungicide.

15. A composition of claim 14 wherein the second plant fungicide is a sterol inhibiting fungicide of the type that inhibits O-14 demethylation.

16. A composition of claim 15 wherein the compound claim 1 is 2,6-dichloro-N-[[4-(trifluoromethyl)phenyl]-methyl]benzamide.

17. A composition of claim 16 wherein the second plant fungicide is propiconazole, nuarimol, or prochloraz.

18. A composition of claim 14 wherein the second plant fungicide is chlorothalonil or benomyl.

19. A composition of claim 18 wherein the compound of claim 1 is 2,6-dichloro-N-[[4-(trifluoromethyl)-phenyl]methyl]benzamide.

20. A fungicidal composition comprising a compound of claim 2 in combination with a phytologically-acceptable inert carrier.

21. A composition of claim 20 in which the compound of claim 2 is 2,6-dichloro-N-[[4-(trifluoromethyl)phenyl]methyl]benzamide.

22. A fungicidal method which comprises applying a fungus inhibiting amount of a compound of claim 2 to the locus of a fungus.

23. A method of claim 22 wherein the compound of claim 1 is 2,6-dichloro-N-[[4-(trifluoromethyl)phenyl]-methyl]benzamide.

24. The method of claim 23 when used to reduce the adverse effects of powdery mildew on a cereal grain crop.

* * * * *